(12) United States Patent
Nakamura

(10) Patent No.: US 6,364,846 B1
(45) Date of Patent: Apr. 2, 2002

(54) TREATING TOOL FOR AN ENDOSCOPE

(75) Inventor: Tsutomu Nakamura, Hino (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/123,736

(22) Filed: Jul. 28, 1998

(30) Foreign Application Priority Data

Aug. 5, 1997 (JP) .............................................. 9-210593
Jun. 9, 1998 (JP) ........................................... 10-160504

(51) Int. Cl.$^7$ .............................................. A61B 10/00
(52) U.S. Cl. ...................... 600/564; 600/101; 606/206
(58) Field of Search ........................ 606/205–211, 167, 606/179, 171, 174, 185, 1, 45–52; 600/562–572, 101

(56) References Cited

U.S. PATENT DOCUMENTS

| D92,210 S | * | 5/1934 | Roy et al. ..................... D7/380 |
| 4,763,668 A | * | 8/1988 | Macek et al. ................ 606/206 |
| 4,815,476 A | | 3/1989 | Clossick |
| 4,982,727 A | * | 1/1991 | Sato ............................ 606/205 |
| 5,609,601 A | * | 3/1997 | Kolesa et al. ............... 606/205 |
| 5,827,323 A | * | 10/1998 | Klieman et al. ............ 606/205 |

FOREIGN PATENT DOCUMENTS

| DE | G 84 18 993.2 | 9/1984 |
| DE | 89 03 111.3 | 8/1989 |
| EP | 0 593 929 A1 | 4/1994 |
| JP | 4-28567 | 7/1992 |

* cited by examiner

Primary Examiner—Glenn K. Dawson
(74) Attorney, Agent, or Firm—Frishauf, Holtz, Goodman, Langer & Chick, P.C.

(57) ABSTRACT

A treating tool for use in combination with an endoscope includes a sheath with a biopsy treating section provided at its distal end and adapted to be rotated with the treating section as one unit, an operation wire inserted in the sheath and adapted to transmit an operation force to the treating section, a treating section open/close operation section for operating the treating section through the operation wire, and a sheath rotation operation section equipped with an operation mechanism for rotating the sheath.

26 Claims, 5 Drawing Sheets

TREATING TOOL FOR AN ENDOSCOPE

BACKGROUND OF THE INVENTION

The present invention relates to a treating tool for an endoscope, such as biopsy forceps and grasping forceps, which is used as an attached tool for the endoscope.

The ordinary biopsy forceps known as a treating tool for the endoscope has a sheath, a pair of cutting-edged cups pivoted to a distal end of the sheath, an operation wire inserted in the sheath, and a proximal operation section for pushing or pulling the operation wire. And the cutting-edged cups are opened and closed by operating the operation wire in the sheath. When a living tissue (sample) in the body cavity of a human being is to be collected by the biopsy forceps, it has been the practice to tear off the tissue portion using the cutting edges by pulling the operation wire with the living tissue grasped by the cups. For this reason, significant damage has been caused to the living body upon picking up the living tissue portion and significant bleeding has occurred. In addition, it has been possible to pick up an amount of tissue portion simply grasped by the cups.

Jpn. UM Appln. KOKOKU Publication No. 4-28567 has proposed biopsy forceps using a coil sheath and twisted operation wire. In this biopsy forceps, the coil sheath and operation wire are mutually oppositely twisted together and cups on the distal end of the coil sheath are rotated by a pull force of the operation wire. And the grasped tissue portion is torn off by the rotation force and is collected as a sample. In this biopsy forceps, however, the rotation state is liable to get unsteady, depending upon the insertion state, etc., of the endoscope. In addition, it is not always possible to secure a rotation force adequate to tear off any living tissue, by the cups, in the body cavity of a human subject.

BRIEF SUMMARY OF THE INVENTION

It is accordingly the object of the present invention to provide a treating tool for an endoscope which can positively collect an amount of tissue necessary to make diagnosis and to achieve this with minimal possible bleeding.

The object of the present invention is achieved by the treating tool for the endoscope as will be set out below. That is, the treating tool includes a treating section for biopsy which is provided at a distal-end side, a sheath rotatable with the treating section as one unit, an operation wire inserted in the sheath and adapted to transmit a force with which the treating section is operated, a first operation section for operating the treating section through the operation and a second operation section equipped with an operation mechanism for rotating the sheath.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments give below, serve to explain the principles of the invention.

DETAILED DESCRIPTION OF THE INVENTION

First Embodiment

Figure 1:
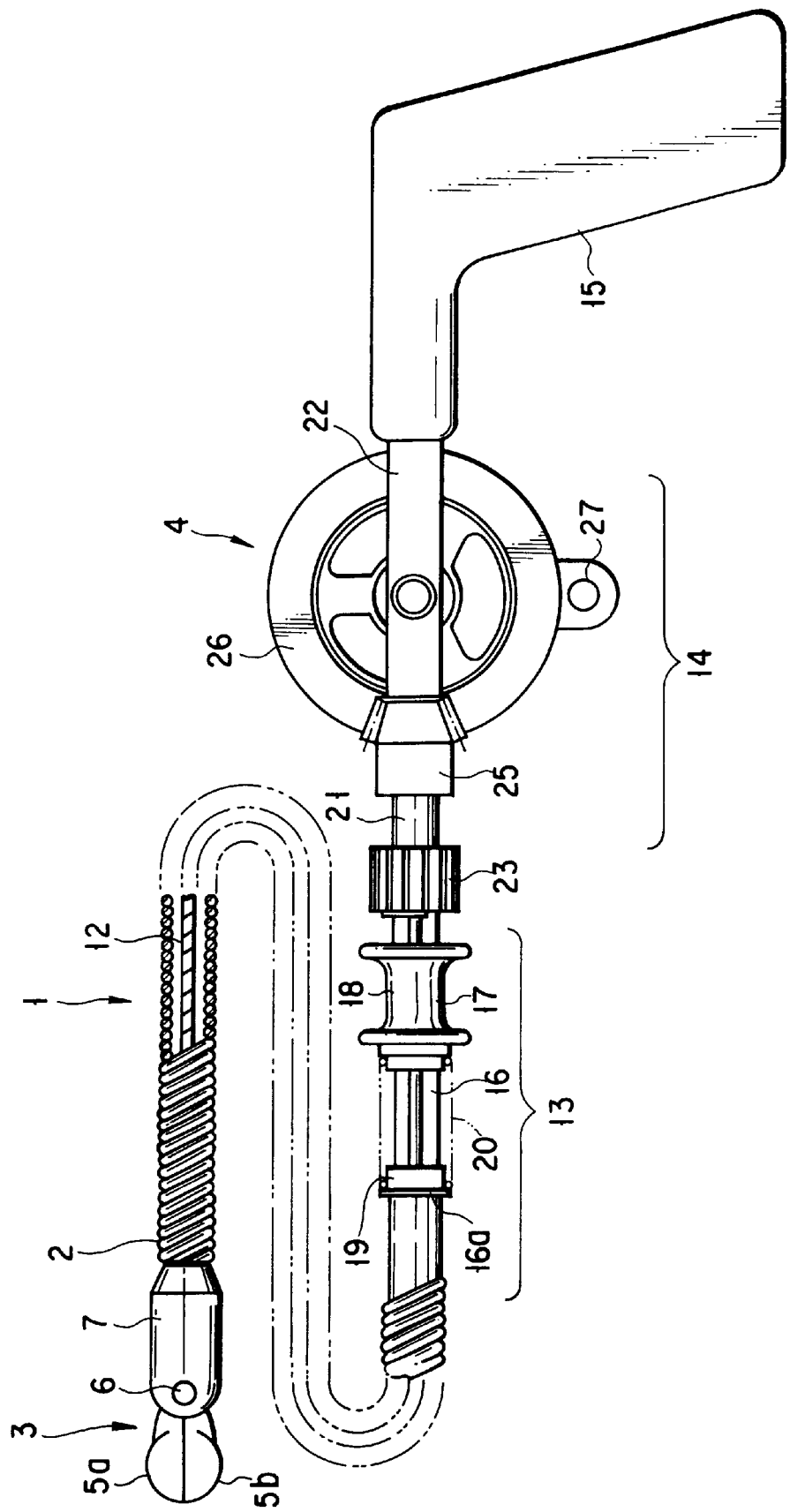
FIG. 1 is a view, partly cut away, showing a biopsy forceps according to a first embodiment of the present invention.

Biopsy forceps of an endoscope's treating tool according to a first embodiment of the present invention will be explained below with reference to FIGS. 1 to 3 of the accompanying drawing.

The biopsy forceps of the first embodiment comprise a sheath composed of a plurality of closely-turned coil elements, a treating section 3 provided on a distal end section of a sheath 2 and an operation section 4 provided at a proximal end section of the sheath 2. The sheath 2 is 0.8 mm to 6 mm in external diameter and is flexible in nature.

The treating section 3 has a pair of biopsy cups 5a, 5b. The biopsy cups 5a, 5b are pivotally supported by a pin 6 on a sleeve-like distal end section 7 which is connected to the distal end section of the sheath 2. As will be set out below, the treating section 3 with the pair of cups 5a, 5b is opened/closed by an operation wire 12 through a link mechanism.

Figure 2:
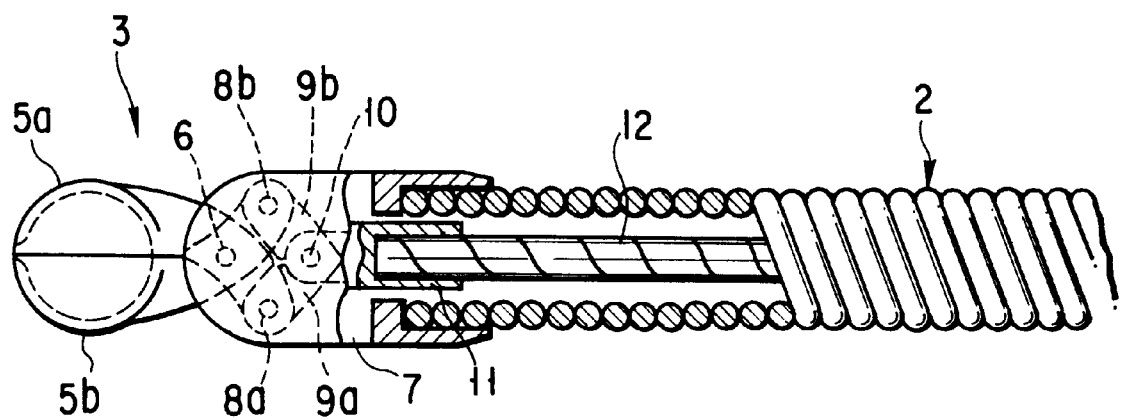
FIG. 2 is a view, partly in cross-section, showing a distal end section and its neighborhood of a biopsy forceps according to a first embodiment of the present invention.
Figure 3:
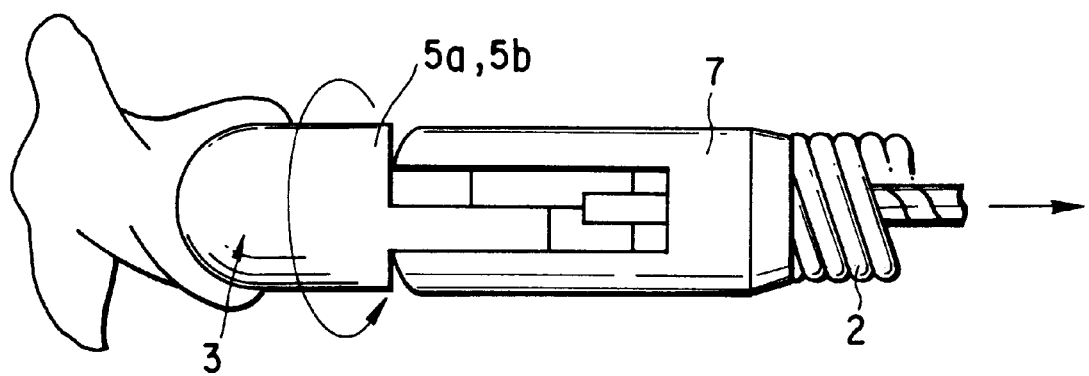
FIG. 3 is an explanatory view for collecting a tissue, in a body cavity of a human subject, with a biopsy forceps according to a first embodiment of the present invention.

As shown in FIG. 2, link plates 9a and 9b have their forward end portions individually attached by pins 8a and 8b to the base portions of the corresponding biopsy cups 5a and 5b. The link plates 9a and 9b have their base portions pivoted by a single pin 10 to a common connection member 11. The base portions of the respective biopsy cups 5a, 5b, respective link plates 9a, 9b and connection member 11 constitute the link mechanism. The link mechanism is opened/closed by the pushing/pulling of the operation wire 12.

The forward end of the operation wire 12 is connected to the connection member 11. The proximal-end side portion of the operation wire 12 extends through the sheath 2 and leads to the operation section 4.

The operation section 4 includes a treatment section's open/close operation section 13, sheath rotation operation section 14 and grip section 15, the open/close operation section 13 serving as a first operation section and the sheath rotation operation section 14 serving as a second operation section.

A slide shaft section 16 is provided at the open/close operation section 13 such that it is fixedly connected to the rear end of the sheath 2. A slider 17 is fitted over the slide shaft section 16 such that it is slidable in an axial direction. The operation wire 12 is connected at its base end to the slider 17. A finger engaging recess 18 is provided at an outer peripheral portion of the slider 17. The finger engaging recess 18 is such that its cross-sectional outer configuration defined orthogonal to the axial direction is substantially circular and provides a natural feeling even if being rotated. When the slider 17 is moved back and forth, the operation wire 12 can be pulled/pushed.

A spring rest ring 19 is fitted over the slide shaft section 16 and stopped in a manner to be latched to a stepped end face 16a of a forward end of the slide shaft 16.

A slider spring 20 is provided between the slider 17 and the spring rest ring 19 and comprised of a coil-like compression spring. The slider spring 20 is urged toward a direction in which the slider 17 is retracted and, by the pulling of the operation wire 12, is energized in a direction in which the biopsy cups 5a, 5b in the treating section 3 are closed. For this reason, the biopsy cups 5a, 5b wait in a closed state. The sheath rotation operation section 14 has a rotation shaft section 21 rotatable relative to the operation shaft body 22. The grip section 15 is connected to a base-side end portion of the operation shaft body 22.

The forward end portion of the rotation shaft section 21 is connected to a rear end section of the slide shaft section 16 in the open/close operation section 13 through the utilization of the coupling means. That is, the forward end of the rotation shaft section 21 is detachably connected to the rear end of the slide shaft section 16 through the utilization of a coupling member 23. The coupling member 23 enables the rear end 16 of the slide shaft section 16 and front end of the rotation shaft section 21 to be coupled together and fitted therein in a coaxially fitted manner and, by doing so, to be fixedly tightened thereby. The coupling member 23 is constituted by, for example, a ring member.

A smaller bevel gear 25 is coaxially mounted on the rear end portion of the rotation shaft section 21. A greater bevel gear 26 is supported on the operation shaft body 22 in a direction perpendicular to the center axis of the rotation shaft section 21 and smaller bevel gear 25. The smaller bevel gear 25 is in mesh with the greater bevel gear 26. The greater bevel gear 26 has a rotation knob 27 for rotationally operating the bevel gear 26. When the greater bevel gear 26 is rotated by the rotation knob 27, then the rotational force of the greater bevel gear 26 is transmitted to the smaller bevel gear 25, so that, through the coupling member 23, the sheath 2 having the open/close operation section 13 and treating section 3 are wholly rotated together with these sections.

The treating section 3 is set normally in a closed state under an energized force of the slider spring 20. With the treating section 3 in a closed state, the biopsy forceps are introduced into a body cavity of a human subject through a channel of an endoscope or trocar. If there exists any tissue or region of interest, the slider 17 is pushed forward against the energized force of the slider spring 20 to push the operation wire 12 forward. Then the biopsy cups 5a, 5b of the treating section 3 are opened through the link mechanism. When the user's finger is released from the slider 17 with the opened cups 5a, 5b pushed against such a tissue or region of interest, then the slider 17 is retracted back under the energized force of the slider spring 20 and the operation wire 12 is pulled back, so that the cups 5a, 5b in the treating section are automatically closed. For this reason, the biopsy cups 5a, 5b grasp the tissue portion. And under the energized force of the slider spring 20 the tissue portion is maintained by the cups 5a, 5b in a grasped state.

Then if, in the sheath rotation operation section 14, the greater bevel gear 26 is rotated by the rotation knob 27, this rotation force is transmitted from the greater bevel gear 26 to the smaller bevel gear 26 to cause the sheath to be rotated as a whole. Then, as shown in FIG. 3, the biopsy cups 5a, 5b with the tissue portion grasped thereby is rotated and hence the grasped tissue portion is twisted and torn off the base of the tissue, so that the torn-off tissue portion is trapped at the closed biopsy cups 5a, 5b.

In this way, since the grasped tissue portion is twisted at the cups 5a, 5b, torn off the base of the tissue and collected as a sample, it is possible to collect a greater volume of a tissue portion than that actually grasped by the biopsy cups 5a, 5b and do this with less bleeding. By this operation at the sheath rotation operation section 14, the sheath 2 is directly rotated together with its treating section 3 and open/close operation section 13 and it is possible to positively obtain a stable rotation force necessary to pick up a tissue portion of a living body cavity.

Second Embodiment

Figure 4:
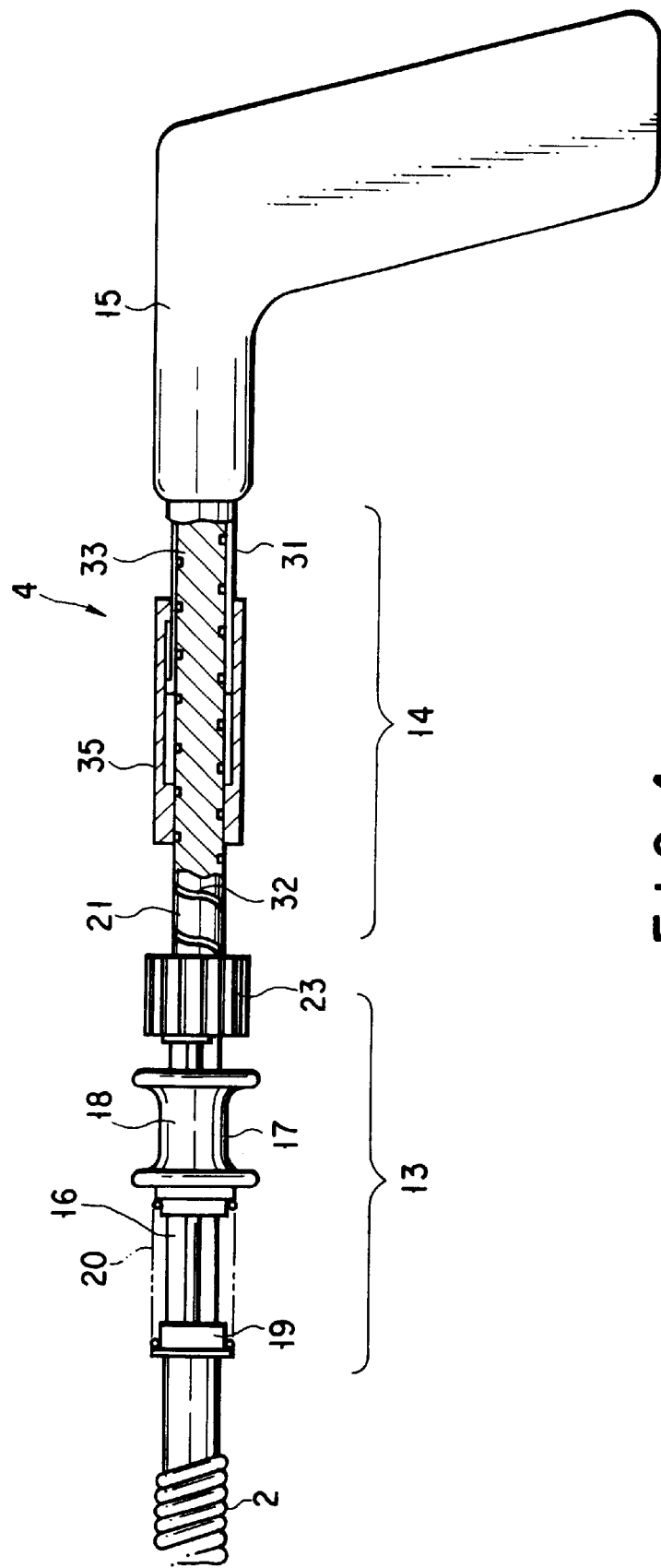
FIG. 4 is a side view, partly in cross-section, showing an operation section of a biopsy forceps according to a second embodiment of the present invention.

A second embodiment of the present invention will be explained below with respect to FIGS. 4 and 5. This embodiment constitutes a variant of the biopsy forceps of the first embodiment.

The explanation is restricted mainly to those different portions or sections with respect to the first embodiment. As in the case of the first embodiment, a rotation shaft section 21 in a sheath rotation operation section 14 is connected by a coupling member 23 to a slide shaft section 16 in a treating section open/close operation section 13. The rotation shaft section 21 is fitted, and rotatably supported, in a cylindrical bearing member 31. A spiral cam groove 32 is provided in the outer periphery of the rotation shaft 21 and, in this case, the rotation shaft section 21 constitutes a cam shaft 33. The bearing member 31 is fixedly mounted in a grip section 15.

Figure 5:
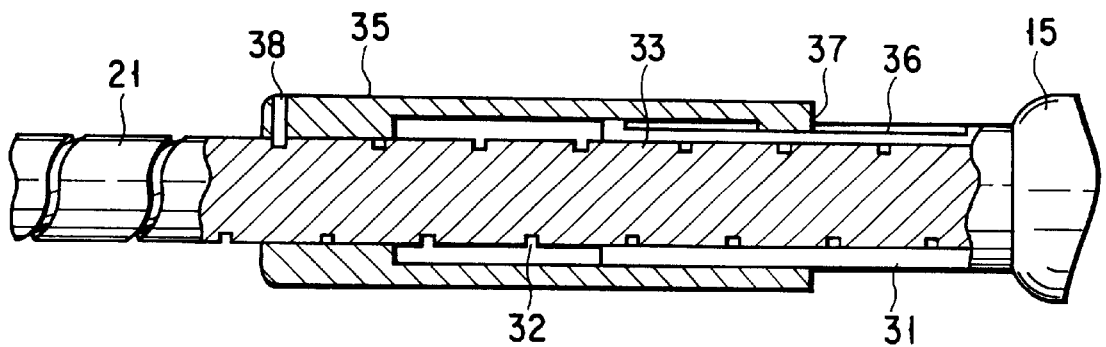
FIG. 5 is a view, partly in longitudinal cross-section, showing a sheath rotation operation section of a biopsy forceps according to the second embodiment of the present invention.

As shown in FIG. 5, a cam follower 35 of the cylindrical member is loosely fitted in the cam shaft 33. The base portion of the cam follower 35 is slidably fitted over the bearing member 31 and so restricted by a guide means as to be moved only in an axial direction. An elongated groove 36 is formed in the outer periphery of the bearing member 31 along an axial direction of the cam shaft 33. The cam follower 35 has a projection 37 which is fitted in the elongated groove 36. For this reason, the cam follower 35 is so guided as to be moved only in the axial direction of the cam shaft 33.

A pin-like projection 38 is formed in the inner wall of the forward end portion of the cam follower 35 to engage with, and be spirally followed along, the cam groove 32 in the cam shaft 33. If the cam follower 35 serving as an operation body is gripped by hand and moved back and forth along the bearing member 31, then the cam shaft 33 can be rotated through the threaded engagement of the projection 38 with the cam groove 32. By doing so, a sheath rotation operation section 14 is provided as in the case of the first embodiment to allow a sheath 2 to be wholly rotated together with its treating section 3 and treatment section's open/close operation section 13.

According to the sheath rotation operation section 14 of the second embodiment, it is possible to construct the sheath rotation operation section 14 with less component parts than in the first embodiment and hence to obtain an effect the same as in the first embodiment.

Third Embodiment

Figure 6:
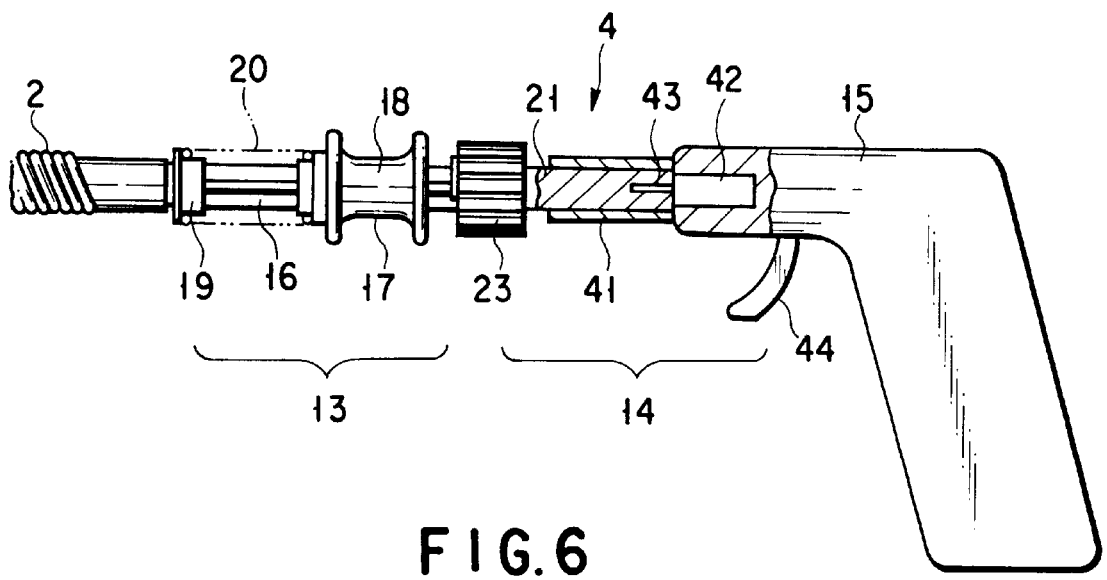
FIG. 6 is a view, partly cut away, showing a sheath rotation operation section of a biopsy forceps according to a third embodiment of the present invention.

A third embodiment of the present invention will be explained below with reference to FIG. 6. The third embodiment constitutes a variant of the biopsy forceps of the first embodiment.

An explanation will be given below mainly about those different portions and sections of this variant with respect to the above-mentioned first embodiment. As shown in FIG. 6, a rotation shaft section 21 in a sheath rotation operation section 14 is connected by a coupling member 23 to a slide shaft section 16 in a treating section open/close operation section 14. The rotation shaft section 21 is rotatably supported by a cylindrical bearing member 41 which is fixedly mounted at a grip section 15. In this way, the rotation shaft section 21 is connected through the bearing member 41 to the grip section 15. A rotation shaft 43 of an actuator 42 is buried in the rear end portion of the rotation shaft 21 and the actuator 42 is arranged in the forward end portion of the grip section 15. As a result, the rotation shaft section 21 and rotation shaft 43 are coupled together as one unit. A switch operation lever 44 is mounted at the grip section 15 and, upon being operated, turns an associated switch ON or OFF, so that the actuator is rendered ON or OFF. By the operation of the operation lever 44 the actuator 42 is driven to allow the rotation shaft section 21 and hence the whole sheath 2 to be rotated as in the case of the first embodiment.

By gripping the grip section 15 by one hand of the operator and simply operating the switch operation lever 44 with his or her finger it is possible to rotate the whole sheath 2 and hence its treating section 3 and treating section open/close operation section 13 and do this by a simpler operation than in the second embodiment. It is, therefore, possible to obtain the same advantage as in the first and second embodiment.

Fourth Embodiment

Figure 7:
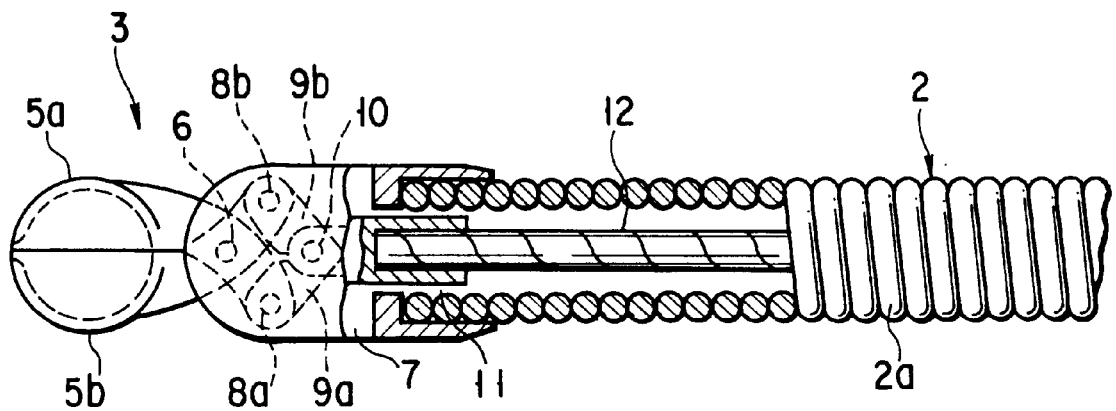
FIG. 7 is a side view, partly cut away, showing a distal end section and its neighborhood of a biopsy forceps according to a fourth embodiment of the present invention.

A fourth embodiment will be explained below with reference to FIG. 7. The fourth embodiment constitutes a variant of the first embodiment. A sheath 2 of biopsy forceps 1 is comprised of a closely-turned single-coil structure. The other structure is the same as in the first embodiment.

When, in a sheath rotation operation section 14, a greater bevel gear 26 is rotated by a rotation knob 27, its rotation force is transmitted from the greater level gear 26 to a smaller bevel gear 25 and hence to the sheath 2, but this rotation force is not transmitted directly to biopsy cups 5a, 5b of the treating section 3. Instead, the rotation force is stored up in the closely-turned single-coil structure constituting the sheath 2. At a time when a rotation force is highly stored up to a level exceeding a given rotation number, a resultant rotation force is released, so that it is transmitted all at once to the treating section 3. For this reason, it provides a force great enough to tear off a living body tissue portion grasped by biopsy cups 5a, 5b.

Fifth Embodiment

Figure 8:
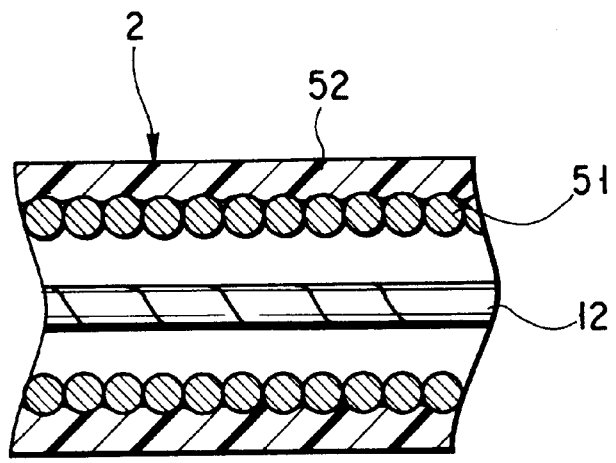
FIG. 8 is a longitudinal cross-sectional view showing a sheath section of a biopsy forceps according to a fifth embodiment of the present invention.

A fifth embodiment will be explained below with reference to FIG. 8. The fifth embodiment constitutes a variant of the first embodiment. A sheath 2 of biopsy forceps 1 comprises a sheath unit 51 comprised of a closely-turned multi-coil or single-coil structure and a tube-like resin outer covering provided on the outer periphery of the sheath unit 51. The inner surface of the outer covering 52 is intimately seated on the uneven outer surface of the coil structure or sheath unit 51. As a material for the outer covering 52 use is made of a fluorine-series resin, polyethylene, vinyl chloride, polyurethane, etc. The other structure of this embodiment is the same as in the first embodiment.

By covering, with the outer covering 52, the outer peripheral surface of the sheath unit 51 comprised of the multi-coil or single-coil it is possible to improve the transmission capability of a rotation force of the sheath 2.

Additional advantages and modifications will readily occurs to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treating tool for use in combination with an endoscope, comprising:
    a sheath having a distal end with a living tissue target treating section provided thereon;
    an operation wire having a distal end and a proximal end, and being inserted in the sheath to transmit a treating section operation force to the treating section;
    a first operation section which operates the treating section through the operation wire;
    an urging member which maintains a state of the treating section relative to a living tissue; and
    a second operation section, equipped with an operation mechanism, which rotates the sheath at a high speed while allowing the urging member to maintain the state of the treating section relative to the living tissue;
    wherein the second operation section includes a rotatable shaft member connected to the sheath and having a spiral cam in an outer periphery thereof and a cam follower set in engagement with the cam and adapted to slide in an axial direction of the shaft member, wherein by a moving operation of the cam follower in the axial direction of the shaft member, the shaft member is rotated and the sheath is rotated.

2. A treating tool according to claim 1, wherein the first operation section includes a slider connected to a rear end portion of the operation wire and a side shaft member for guiding the slider.

3. A treating tool according to claim 2, wherein the urging member comprises a compression spring for energizing the slider in a direction to close the treating section for collecting a living tissue sample, and normally sets the treating section in a closed state under an energizing force of the compression spring.

4. A treating tool according to claim 1, wherein the sheath comprises a plurality of closely-turned coil elements.

5. A treating tool according to claim 1, wherein the sheath comprises a single-coil structure.

6. A treating tool according to claim 1, wherein, by an operation of the second operation section, the sheath allows a rotation force to be stored up to a given extent and, upon exceeding that extent, transmits a corresponding rotation force all at once.

7. A treating tool according to claim 1, wherein the second operation section, together with the first operation section, rotates the sheath.

8. A treating tool according to claim 1, wherein the sheath comprises a coil member and an outer covering of a resin provided on an outer periphery of the coil member and wherein the sheath enhances a transmission force with which the rotation of the sheath is transmitted.

9. A treating tool according to claim 8, wherein the coil member has an uneven outer peripheral surface and the outer covering of the resin is deeply and intimately seated on the uneven outer peripheral surface of the coil member.

10. A treating tool according to claim 1, wherein the treating section comprises a pair of cups for grasping a living tissue and collecting a living tissue portion.

11. A treating tool according to claim 1, wherein an outer cross-section configuration of the first operation section taken in a direction perpendicular to an axial direction thereof is substantially circular.

12. A treating tool according to claim 1, further comprising a connector that detachably connects the first and second operation sections to each other.

13. A treating tool for use in combination with an endoscope, comprising:
   a sheath having a distal end with a living tissue target treating section provided thereon;
   an operation wire having a distal end and a proximal end, and being inserted in the sheath to transmit a treating section operation force to the treating section;
   a first operation section which operates the treating section through the operation wire;
   an urging member which maintains a state of the treating section relative to a living tissue; and
   a second operation section, equipped with an operation mechanism, which rotates the sheath while allowing the urging member to maintain the state of the treating section relative to the living tissue;
   wherein the second operation section includes a rotatable shaft member connected to the sheath and having a spiral cam in an outer periphery thereof and a cam follower set in engagement with the cam and adapted to slide in an axial direction of the shaft member, wherein by a moving operation of the cam follower in the axial direction of the shaft member, the shaft member is rotated and the sheath is rotated.

14. A treating tool for use in combination with an endoscope, comprising:
   a sheath having a distal end with a living tissue target treating section provided thereon;
   an operation wire having a distal end and a proximal end, and being inserted in the sheath to transmit a treating section operation force to the treating section;
   a first operation section which operates the treating section through the operation wire;
   an urging member which maintains a state of the treating section relative to a living tissue;
   a second operation section which is located at a proximal end of the first operation section and which rotates said sheath around an axis of said sheath, said second operation section including a first gear that is coupled to said sheath and that is coaxially mounted on a shaft of said sheath, a second gear that meshes with said first gear and that has a rotation axis of which is substantially perpendicular to said sheath, and a rotation knob that is coupled to said second gear for rotating said second gear; and
   a grip for gripping the treating tool when the first and second operation sections are operated,
   wherein, when said rotation knob is rotated, rotation of said second gear is transmitted to said first gear, thereby causing both said and said living tissue target treating section provided on the distal end of said sheath to rotate.

15. A treating tool for use in combination with an endoscope, according to claim 14, wherein said second gear is larger than said first gear, and said first gear is rotatable by said second gear at a high speed.

16. A treating tool according to claim 14, wherein the first operation section includes a slider connected to a rear end portion of the operation wire and a side shaft member for guiding the slider.

17. A treating tool according to claim 16, wherein the urging member comprises a compression spring for energizing the slider in a direction to close the treating section for collecting a living tissue sample, and normally sets the treating section in a closed state under an energizing force of the compression spring.

18. A treating tool according to claim 14, wherein the sheath comprises a plurality of closely-turned coil elements.

19. A treating tool according to claim 14, wherein the sheath comprises a single-coil structure.

20. A treating tool according to claim 14, wherein, by an operation of the second operation section, the sheath allows a rotation force to be stored up to a given extent and, upon exceeding that extent, transmits a corresponding rotation force all at once.

21. A treating tool according to claim 14, wherein the second operation section, together with the first operation section, rotates the sheath.

22. A treating tool according to claim 14, wherein the sheath comprises a coil member and an outer covering of a resin provided on an outer periphery of the coil member, and wherein the sheath enhances a transmission force with which the rotation of the sheath is transmitted.

23. A treating tool according to claim 22, wherein the coil member has an uneven outer peripheral surface and the outer covering of the resin is deeply and intimately seated on the uneven outer peripheral surface of the coil member.

24. A treating tool according to claim 14, wherein the treating section comprises a pair of cups for grasping a living tissue and collecting a living tissue portion.

25. A treating tool according to claim 14, wherein an outer cross-section configuration of the first operation section taken in a direction perpendicular to an axial direction thereof is substantially circular.

26. A treating tool according to claim 14, further comprising a connector that detachably connects the first and second operation sections to each other.

* * * * *